United States Patent
Korfhage et al.

(10) Patent No.: US 11,220,705 B2
(45) Date of Patent: Jan. 11, 2022

(54) METHOD FOR IMMOBILIZING A NUCLEIC ACID MOLECULE ON SOLID SUPPORT

(71) Applicant: QIAGEN GmbH, Hilden (DE)

(72) Inventors: Christian Korfhage, Hilden (DE); Evelyn Fricke, Hilden (DE)

(73) Assignee: QIAGEN GmbH, Hilden (DE)

( * ) Notice: Subject to any disclaimer, the term of this patent is extended or adjusted under 35 U.S.C. 154(b) by 434 days.

(21) Appl. No.: 15/567,563

(22) PCT Filed: Apr. 25, 2016

(86) PCT No.: PCT/EP2016/059164
§ 371 (c)(1),
(2) Date: Oct. 18, 2017

(87) PCT Pub. No.: WO2016/170179
PCT Pub. Date: Oct. 27, 2016

(65) Prior Publication Data
US 2018/0112251 A1    Apr. 26, 2018

(30) Foreign Application Priority Data
Apr. 24, 2015 (EP) .................................... 15164961

(51) Int. Cl.
C12P 19/34       (2006.01)
C12Q 1/6806     (2018.01)
C12Q 1/6844     (2018.01)

(52) U.S. Cl.
CPC ......... *C12Q 1/6806* (2013.01); *C12Q 1/6846* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,641,658 A | 6/1997 | Adams et al. | |
| 5,700,642 A * | 12/1997 | Monforte | C12Q 1/6816 |
| | | | 435/6.12 |
| 6,300,070 B1 | 10/2001 | Boles et al. | |
| 7,115,400 B1 | 10/2006 | Adessi et al. | |
| 7,790,418 B2 | 9/2010 | Mayer | |
| 7,972,820 B2 | 7/2011 | Mayer | |
| 9,360,526 B2 * | 6/2016 | Vogelstein | A61P 9/10 |
| 2002/0012933 A1 | 1/2002 | Rothberg et al. | |
| 2002/0150899 A1 * | 10/2002 | Fu | C12N 15/1096 |
| | | | 435/6.16 |
| 2003/0148344 A1 | 8/2003 | Rothberg et al. | |

(Continued)

FOREIGN PATENT DOCUMENTS

| | | |
|---|---|---|
| WO | 2013/028643 A1 | 2/2013 |
| WO | 2014/020154 A1 | 2/2014 |
| WO | 2014/026031 A1 | 2/2014 |

OTHER PUBLICATIONS

Primosome from Wikipedia. Printed on Oct. 8, 2020.*

(Continued)

*Primary Examiner* — Frank W Lu
(74) *Attorney, Agent, or Firm* — Seed IP Law Group LLP

(57) ABSTRACT

The present invention is directed to a method for immobilizing nucleic molecule on solid support and to a use of a nucleic acid non-immobilized primer in combination with a nucleic acid primer linked to a solid support in said method.

21 Claims, 5 Drawing Sheets

Figure 1:
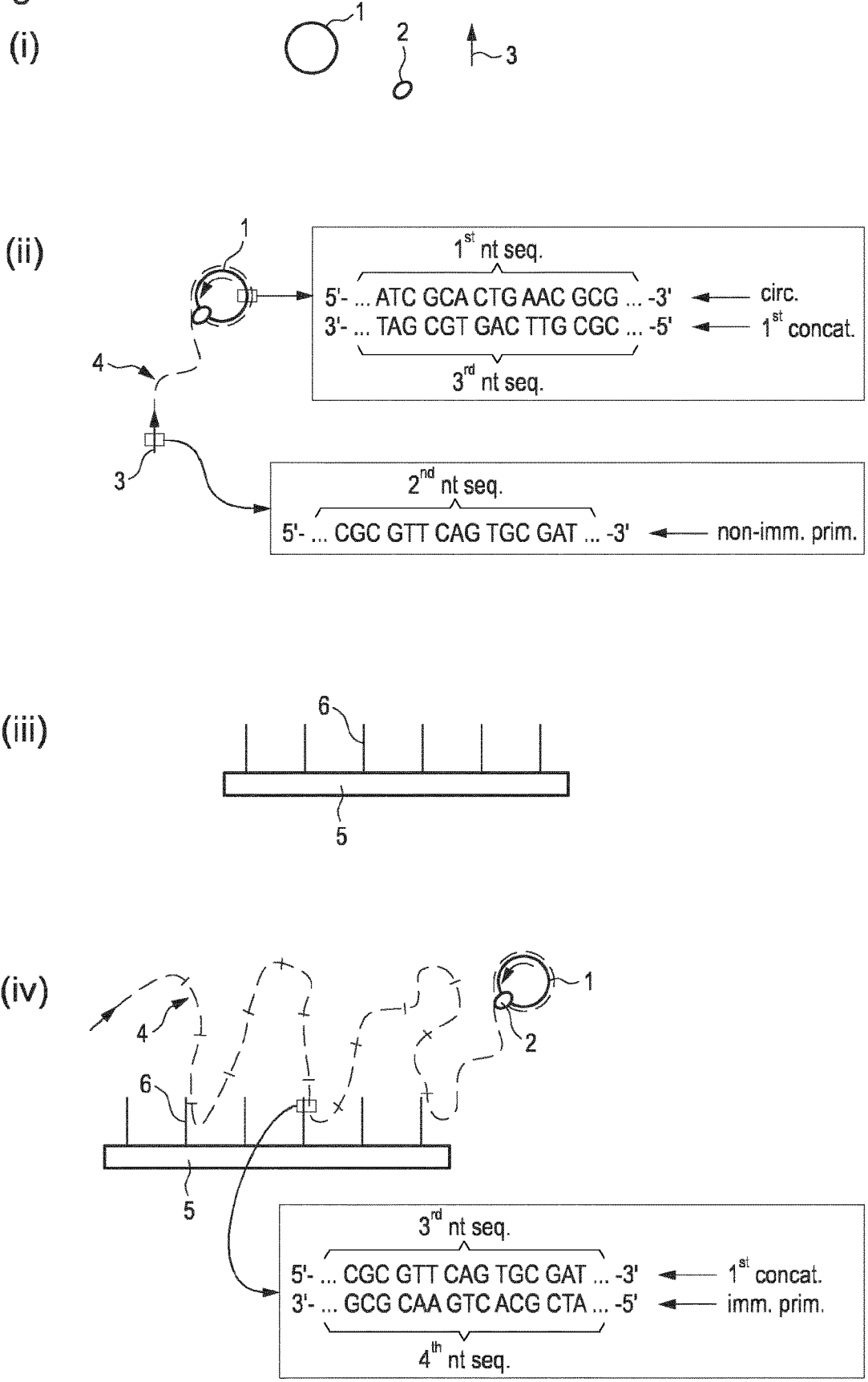
Figure 1:
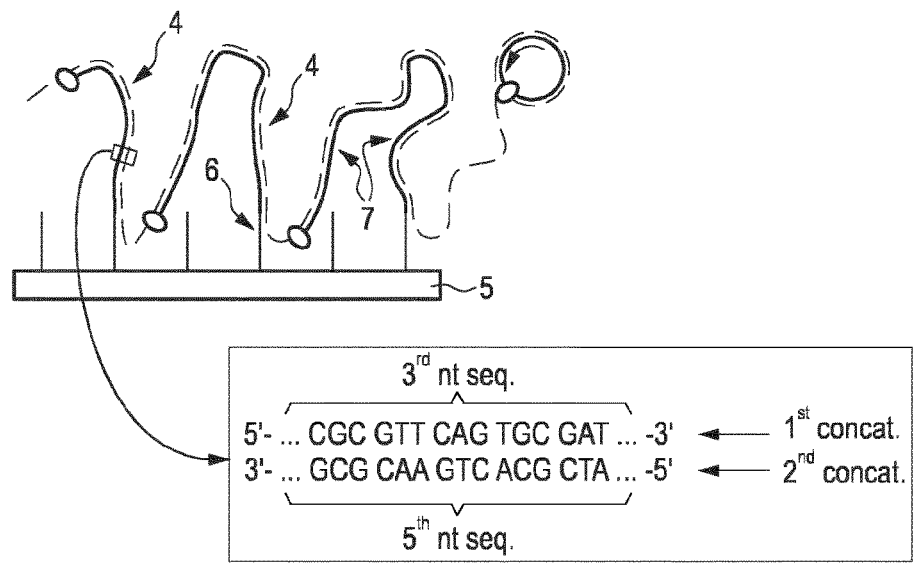
Figure 1:
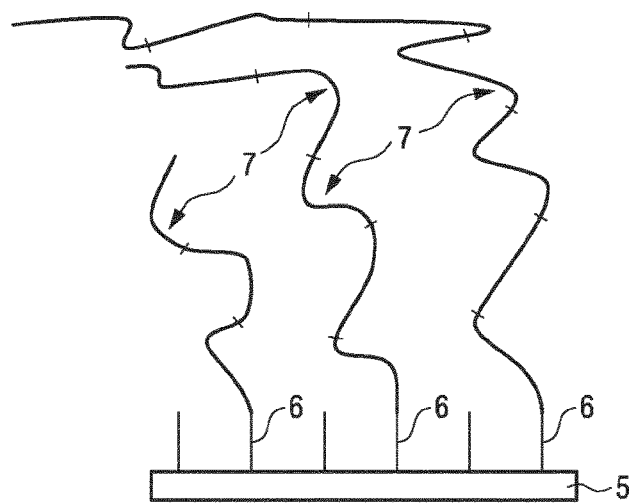
Figure 1:
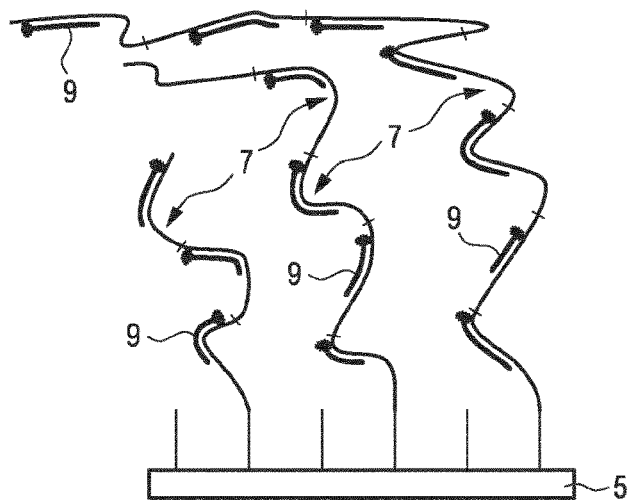

Specification includes a Sequence Listing.

(56) References Cited

U.S. PATENT DOCUMENTS

| | | |
|---|---|---|
| 2004/0132061 A1 | 7/2004 | Quinn et al. |
| 2004/0152212 A1* | 8/2004 | Huang .................... B82Y 5/00 436/518 |
| 2007/0190548 A1 | 8/2007 | Lee et al. |
| 2008/0160580 A1 | 7/2008 | Adessi et al. |
| 2009/0018024 A1 | 1/2009 | Church et al. |
| 2009/0156412 A1 | 6/2009 | Boyce, IV et al. |
| 2010/0008939 A1 | 1/2010 | Nelson et al. |
| 2010/0022412 A1 | 1/2010 | Rigatti et al. |
| 2010/0075328 A1 | 3/2010 | Bjornson et al. |
| 2010/0316998 A1 | 12/2010 | Gefter |
| 2011/0195457 A1 | 8/2011 | Nelson et al. |
| 2012/0156728 A1 | 6/2012 | Li et al. |
| 2012/0178638 A1 | 7/2012 | Damha et al. |
| 2012/0289426 A1 | 11/2012 | Roos et al. |
| 2013/0296172 A1 | 11/2013 | Fu et al. |
| 2015/0045254 A1 | 2/2015 | Jack |
| 2017/0204459 A1 | 7/2017 | Barany et al. |

OTHER PUBLICATIONS

Adessi et al., "Solid phase DNA amplification: characterisation of primer attachment and amplification mechanisms," *Nucleic Acids Res.* 28(20):e87 (8 pages) (2000).

Barbee et al., "Fabrication of DNA polymer brush arrays by destructive micropatterning and rolling-circle amplification," *Macromol. Biosci.* 11(5):607-617, 2011, (20 pages).

Bentley et al., "Accurate whole human genome sequencing using reversible terminator chemistry," *Nature* 456(7218):53-59, 2008, (21 pages).

Bronner et al., "Improved Protocols for Illumina Sequencing," *Current Protocols in Human Genetics* 80:18.2.1-18.2.42 (Jan. 23, 2014).

Dean et al., "Rapid amplification of plasmid and phage DNA using Phi29 DNA polymerase and multiply-primed rolling circle amplification," *Genome Research* 11(6):1095-1099 (2001).

Gao et al., "Secondary structure effects on DNA hybridization kinetics: a solution versus surface comparison," *Nucleic Acids Res.* 34(11):3370-3377 (2006).

Ju et al., "Four-color DNA sequencing by synthesis using cleavable fluorescent nucleotide reversible terminators," *Proc. Natl. Acad. Sci. USA* 103(52):19635-19640 (2006).

Lane et al., "Amplicon secondary structure prevents target hybridization to oligonucleotide microarrays," *Biosensors and Bioelectronics* 20(4):728-735 (2004).

Nallur et al., "Signal amplification by rolling circle amplification on DNA microarrays," *Nucleic Acids Res.* 29(23):e118 (9 pages) (2001).

New England Biolabs, "9° $N_m$™ DNA Polymerase," https://www.neb.com/products/m0260-9nm-dna-polymerase, Retrieved from the Internet Nov. 3, 2013, 3 pages.

Sekar et al., "Comparative study of sequence-dependent hybridization kinetics in solution and on microspheres," *Nucleic Acids Res.* 33(1):366-375 (2005).

Yi et al., "Molecular Zipper: a fluorescent probe for real-time isothermal DNA amplification," *Nucleic Acids Res.* 34(11):e81 (5 pages) (2006).

Zhao et al., "Massively parallel display of genomic DNA fragments by rolling-circle amplification and strand displacement amplification on chip," *Talanta* 82(2):477-482 (Jul. 15, 2010).

Malhotra et al., "Molecular Methods in Microbiology and their Clinical Application," Journal of Molecular and Genetic Medicine 8(4):1000142 (9 pages) (2014).

AlkD, *Wikipedia*, (2 pages) printed on Aug. 30, 2020.

DNA glycosylase, *Wikipedia*, (12 pages) printed on Aug. 30, 2020.

Multiple displacement amplification, *Wikipedia*, (6 pages) printed on Aug. 30, 2020.

\* cited by examiner (v)

(vi)

(vii)

A

B

A

B

METHOD FOR IMMOBILIZING A NUCLEIC ACID MOLECULE ON SOLID SUPPORT

STATEMENT REGARDING SEQUENCE LISTING

The Sequence Listing associated with this application is provided in text format in lieu of a paper copy, and is hereby incorporated by reference into the specification. The name of the text file containing the Sequence Listing is 770025_479USPC_SEQUENCE_LISTING.txt. The text file is 2.0 KB, was created on Mar. 5, 2020, and is being submitted electronically via EFS-Web.

The present invention is directed to a method for immobilizing a nucleic molecule on a solid support and to a use of a nucleic acid non-immobilized primer in combination with a nucleic acid primer linked to a solid support in said a method.

FIELD OF THE INVENTION

The present invention relates to the field of molecular biology, more particularly to the immobilization of nucleic acid molecules to solid supports.

BACKGROUND OF THE INVENTION

In the field of molecular or recombinant biology for many tasks it is necessary to immobilize a large number of DNA molecules on surfaces.

One prominent example requiring large numbers of DNA molecules immobilized on surfaces are high simultaneous or massive parallel sequencing proceedings. There, for the immobilization at first a DNA library is produced. For this purpose, DNA, such as genomic or cDNA, is cut into small linear fragments. The DNA fragments are provided at their ends with adaptor sequences. The central section located between the adapter sequences comprises the DNA which is used for the DNA library preparation. Among all fragments the central sections ideally have low sequence length variability. The actual length of the sequence of the central section depends on the application. For example, for massive parallel sequencing proceedings a length of approximately 200 to 500 bp is preferred. In other applications different lengths may be used.

The DNA fragments of the DNA library are hybridized via at least one of the adaptor sequences to oligonucleotides which were immobilized on a surface. The spacing between the individual hybridization locations can have a random distribution or may be determined via a gridded surface or beads. However, since the individual DNA fragments need to be amplified on the surface the spacing must be as such that after the amplification the individual discrimination remains possible.

In order to produce a sufficiently high number of copies of the DNA fragments to allow a detection or the sequencing on a small panel element, e.g. of a diameter of 1 μm, an amplification of the sequence is carried out.

There are different methods available for the amplification of the individual DNA fragments immobilized on the solid support. These include the method of the so-called bridge amplification as disclosed in U.S. Pat. Nos. 5,641,658, 6,300,070, 7,115,400, 7,790,418, 7,972,820, and Adessi et al. (2000), Solid Phase DNA amplification: characterization of primer attachment and amplification mechanism, Nucleic Acids Res. 2000 Oct. 15 28(20):E87. Another method is the so-called Wildfire Amplification as disclosed in US 2012/0156728. Among these methods is the so-called Rolling Circle Amplification, as disclosed in US 2002/0012933, US 2003/0148344, Barbee et al. (2011), Fabrication of DNA Polymer Brush Arrays by Destructive Micropatterning and Rolling-Circle Amplification, Macromol. Biosci. 2011 12, 11(5):607-17, and Nallur et al. (2001), Signal amplification by rolling circle amplification on DNA microarrays, Nucleic Acids Res. 2001, 29(23):E118.

However, the existing methods used for immobilizing and amplifying nucleic acid molecules on a solid support are characterized by complex procedural steps, high error susceptibility and, thus, by a low effectiveness and practicability.

Against this background, it is an object of the present invention to provide a method for immobilizing a nucleic acid molecule on a solid support which allows its amplification on the solid support, and which reduces or avoids the problems associated with the prior art methods.

The present invention satisfies these and other needs.

SUMMARY OF THE INVENTION

The present invention provides a method for immobilizing a nucleic acid molecule on a solid support, comprising:
i) providing a reaction mixture comprising
   at least one circular nucleic acid template having a first nucleotide target sequence;
   at least one strand displacement polymerase;
   deoxynucleoside triphosphates (dNTPs);
   reaction buffer, and
   either
   at least one nucleic acid non-immobilized primer having a second nucleotide sequence, said second nucleotide sequence being complementary to at least a segment of said first nucleotide target sequence,
   and/or
   at least one primase;
ii) incubating said reaction mixture under conditions allowing
   said primase, if applicable, to generate said at least one nucleic acid non-immobilized primer having said second nucleotide sequence,
   and/or
   said at least one nucleic acid non-immobilized primer to anneal to said at least one circular nucleic acid template, and
   said strand displacement polymerase to synthesize at least one first nucleic acid concatemeric amplification product by extending said least one nucleic acid non-immobilized primer by rolling circle amplification (RCA), said at least one first nucleic acid concatemeric amplification product comprises multiple copies of a third nucleotide sequence in a head-to-tail orientation, said third nucleotide sequence being complementary to at least a segment of said first nucleotide target sequence;
iii) providing at least one first nucleic acid immobilized primer having a fourth nucleotide sequence linked to a solid support, said fourth nucleotide sequence being complementary to at least a segment of said third nucleotide sequence;
iv) allowing said at least one first nucleic acid concatemeric amplification product to anneal to said at least one first nucleic acid immobilized primer to obtain at least one first nucleic acid concatemeric amplification product-first nucleic acid immobilized primer complex immobilized to said solid support.

The inventors have developed a new method for immobilizing a nucleic acid molecule on a solid support which involves exponential isothermal rolling circle amplification (RCA) which has numerous advantages over the currently used methods in the art.

As used herein, "immobilizing" or "immobilization" refers to a fixing in place of said nucleic acid molecule, in particular to said solid support or its surface, respectively. Said fixing is realized e.g. by a hybridization reaction between two nucleic acid molecules comprising nucleotide sequences being at least partially complimentary to each other, thereby forming a duplex, by a streptavidin-biotin interaction, a covalent bond or a strong ionic bond.

As used herein, a "nucleic acid" or "nucleic acid molecule" may be generally either DNA or RNA, single- or double-stranded, linear or circular, unless specified otherwise.

As used herein, "circular nucleic acid template" refers to a nucleic acid molecule without any free 3' and/or 5' termini or to a nucleic acid molecule where the 3' and 5' intramolecular termini were previously covalently linked to each other, thereby conferring the nucleic acid template a ring- or loop-like or similar structure. The term "template" indicates that the circular nucleic acid molecule encodes a nucleotide target sequence intended to be immobilized to the solid support. The circular nucleic acid template is present in the reaction mixture in a mobile and non-immobilized form.

The circular nucleic acid template can either be artificially produced or may be a naturally occurring DNA. Artificially produced circles are circular nucleic acid molecules which were manipulated or produced by in vitro, e.g. by involving the activities of ligases, polymerases, nucleases etc. Nucleic acid circles can also be isolated or purified from nature, i.e. organisms or the environment, e.g. soil, water, air etc. Common methods for the isolation of naturally occurring circular nucleic acid molecules are well-known to the skilled person. The circular nucleic acid template can be subjected to the reaction mixture either directly after synthesis or isolation or after it has been purified. The purification can comprise one or several steps of physically, chemically, enzymatically or another type.

As used herein, the term "nucleotide" refers to the monomers, or subunits, of nucleic acids like DNA and RNA. Nucleotide may be synonymously used for nucleoside or nucleoside (mono-, di-, tri-) phosphate, and includes the deoxyribose derivatives, i.e. the dNTPs.

As used herein, a "nucleotide sequence" refers to a catenation of nucleotides by phosphodiester bridges.

As used herein, said "first nucleotide target sequence" refers to any nucleotide sequence of interest comprised by the at least one circular nucleic acid template, which is intended to be immobilized on said solid support, either as-such or directly, respectively, or in form of the complimentary nucleotide sequence.

As used herein, "a segment" of a nucleic acid molecule or a nucleotide sequence refers to a section of said molecule or sequence representing ≥10%, ≥15%, ≥20%, ≥25%, ≥30%, ≥35%, ≥40%, ≥45%, ≥50%, ≥60%, ≥70%, ≥80%, ≥90%, ≥100% of the length of the entire nucleic acid molecule, or ≥5 nt, ≥10 nt, ≥15 nt, ≥20 nt, ≥25 nt, ≥30 nt, ≥35 nt, ≥40 nt, ≥45 nt, ≥50 nt, ≥60 nt, ≥70 nt, ≥80 nt, ≥90 nt, ≥100 nt of the nucleotide sequence.

As used herein, "partially complementary" means a nucleotide sequence which is sufficiently complementary to the referring sequence, thereby allowing a hybridization reaction between such sequences. Such partially complementary nucleotide sequences can be ≥50%, preferably ≥60%, more preferably ≥70%, more preferably ≥80%, more preferably ≥90%, more preferably ≥95%, more preferably ≥99%, or 100% complementary to each other.

As used herein, "strand displacement polymerase" refers to a nucleic acid or DNA polymerase with the ability to displace downstream DNA encountered during synthesis. Examples of strand displacement polymerases are φ29 DNA polymerase, Bst DNA polymerase, large fragment, deep Vent$_R$™ DNA polymerase, deep Vent$_R$™ (exo-) DNA polymerase, Klenow Fragment (3'→5' exo-), DNA polymerase I, large (Klenow) fragment, M-MuLV reverse transcriptase, Vent$_R$® DNA polymerase, Vent$_R$® (exo-) DNA polymerase, Bsu polymerase.

As used herein, "deoxynucleoside triphosphates (NTPs)" refer to a mixture of dNTPs such as a conventional mixture of the deoxynucleoside triphosphates dATP, dGTP, dCTP, dTTP, dTTP, dUTP, including modified variants thereof, i.e. the building-blocks for the DNA polymerase to synthesize a new DNA strand.

As used herein, a "reaction buffer" refers to such a buffer solution allowing the functioning of the stranded displacement polymerase and, if applicable, of the primase and, thus, the generation of the at least one first nucleic acid concatemeric amplification product.

Said "nucleic acid non-immobilized primer" refers to a oligonucleotide molecule which is freely suspended in the reaction mixture in a mobile or non-immobilized form, respectively. The primer serves as the starting point for the synthesis of the first nucleic acid concatemeric amplification product. Said nucleic acid non-immobilized primer comprises a "second nucleotide sequence". Said second nucleotide sequence is complimentary to at least a segment of said first nucleotide sequence comprised by said circular nucleic acid template allowing the annealing of the latter by a specific hybridization reaction to the nucleic acid non-immobilized primer. Besides said second nucleotide sequence, the nucleic acid non-immobilized primer may have other sequences.

As used herein, a "primase" refers to a polymerase that catalyzes a short DNA or RNA segment, i.e. the nucleic acid non-immobilized primer, comprising a nucleotide sequence which is at least partially complimentary to said first nucleotide sequence. Using a primase has the advantage that no nucleic acid non-immobilized primer has to be provided as the latter will be synthesized by the primase directly hybridized on the circular nucleic acid template in the reaction mixture.

As used herein, said "first nucleic acid concatemeric amplification product" refers to a nucleic acid molecule consisting of multiple copies of a "third nucleotide sequence" in a head-to-tail orientation. Said concatemeric amplification product is the result of the 'rolling circle amplification' (RCA). In the RCA the circular nucleic acid template rolls or rotates during the amplification reaction and thereby continuously serves as a template in the process of the primer extension until the rolling of the circle is stopped. As a result, the resulting amplification product is consisting of a plurality of third nucleotide sequences which are complimentary to the first nucleotide sequence of the circular nucleic acid template. In this context, "head-to-tail" orientation means that multiple copies of said third nucleotide sequences are linked to each other as follows: . . . 5'-3' 5'-3' 5'-3' 5'-3' 5'-3' . . . (→→). After a short RCA reaction period the rolling circle is stripped-off from the concatemeric amplification product by the strand displacement function of the strand displacement polymerase.

As used herein, a "solid support" refers to any support comprising a surface which may be planar or curved and being capable of receiving and linking nucleic acid molecules. Solid supports of all kinds typically used in the field of immobilization of nucleic acid molecules are encompassed, such as planar chips, beads, capillaries etc. The support may be made of metal, glass, silica, plastics etc. It may also comprise a coated surface. The solid support may also comprise a soft and/or flexible surface.

As used herein, said "first nucleic acid immobilized primer" refers to an oligonucleotide molecule which is linked to the surface of the solid support, either covalently or non-covalently. The first nucleic acid immobilized primer is preferably linked to the solid support via its 5' terminus making its 3' terminus available for a primer extension reaction. The first nucleic acid immobilized primer can be referred to as an "anchor molecule" as it anchors the first and second concatemeric amplification products to the solid support.

Said first nucleic acid immobilized primer comprises a "fourth nucleotide sequence". The fourth nucleotide sequence is complimentary to at least a segment of said third nucleotide sequence. As a consequence, the fourth nucleotide sequence corresponds—at least in parts—to said first nucleotide sequence of said circular nucleic acid template allowing the annealing of the third nucleotide sequence to the fourth nucleotide sequence by a hybridization reaction. The resulting hybridization product is referred to as "first nucleic acid concatemeric amplification product-first nucleic acid immobilized primer complex". Besides the fourth nucleotide sequence, the first nucleic acid immobilized primer may comprise other nucleotide sequences.

The hybridization reaction generally and in the method according to the invention requires conditions well-known to the skilled person depending on the temperature, the pH value, the salt conditions, the concentration of the nucleic acid molecules in the reaction mixture, there lengths, GC contents, nucleotide sequences etc.

"At least one", as used herein, refers to one entity at the minimum, e.g. one circular nucleic acid template, one nucleic acid non-immobilized primer, one primase etc. However, there can be more than one entity, e.g. two, three, four, five, six, seven, eight, nine, ten, one hundred, one thousand, ten thousand etc. entities.

Unless otherwise specified, the individual steps of the method according to the invention may be carried out sequentially or simultaneously/in parallel, respectively.

The method according to the invention has the advantage that the nucleic acid amplification product is consisting of a concatemer. As a result, the hybridization reaction of the first amplification product is very successful since—in contrast to only one sequence like in the cycle—the many sequences of the concatemer can hybridize with the at least one first nucleic acid immobilized primer. In addition, the first nucleic acid concatemeric amplification product can be anchored on the solid support—in comparison to the circular nucleic acid template—in a more efficient manner since the hybridization of a first copy of the third nucleotide sequence to a specific first nucleic acid immobilized primer is followed by the hybridization of a second, third, fourth copy of the third nucleotide to the neighboring first nucleic acid immobilized primers. Basically, the hybridization of the concatemeric amplification product comprising multiple copies of a nucleotide sequence is more successful than the hybridization of a nucleic acid molecule comprising only one of the copies of the nucleotide sequence by the factor representing the number of copies of this nucleotide sequence being present in the concatemeric amplification product.

The method according to the invention has the advantage that it does not only generate a two-dimensional spreading of the nucleic acid molecules on solid surfaces such as the methods known in the art. In the known methods the nucleic acid molecules are located on the surfaces individually and horizontally. In contrast, with the method according to the invention a three-dimensional spreading of the surface-immobilized nucleic acid molecules is achieved where the nucleic acid molecules are not only arranged on the surface horizontally but also vertically. This results in a higher density of amplified products per unit area.

Advantageously, the isothermal method according to the invention does not require an intervening denaturation step in the amplification as this is the case with non-isothermal methods in the art. This results in an acceleration of the hybridization proceedings.

Further advantageously, the method according to the invention results in an exponential amplification of the nucleic acid molecules directly on the surface of the solid support.

In another embodiment the method according to the invention comprises the following further step:

v) incubating said at least one first nucleic acid concatemeric amplification product-first nucleic acid immobilized primer complex under conditions allowing said strand displacement polymerase to synthesize at least one second nucleic acid concatemeric amplification product by extending said first nucleic acid immobilized primer by multiple displacement amplification (MDA), said at least one second nucleic acid concatemeric amplification product comprises multiple copies of a fifth nucleotide sequence in a head-to-tail orientation, said fifth nucleotide sequence being complementary to at least a segment of said third nucleotide sequence.

Due to the fact that in this further embodiment the first nucleic acid concatemeric amplification product represents a new nucleic acid template, the amplification mode changes from RCA to multiple displacement amplification (MDA). "Multiple displacement amplification" refers to a DNA amplification technique which can rapidly amplify minute amounts of the first nucleic acid concatemeric amplification product to a reasonable quantity for further use. The reaction starts by extending said first nucleic acid immobilized primer. DNA synthesis is carried out by a high fidelity enzyme, such as φ29 DNA polymerase, preferably at a constant temperature. Since the RCA is not been interrupted subsequent to the hybridization of the first nucleic acid concatemeric amplification product to said first nucleic acid immobilized primer, said at least one second nucleic acid concatemeric amplification product will be generated.

Said at least one second nucleic acid concatemeric amplification product comprises multiple copies of a "fifth nucleotide sequence" in a head-to-tail orientation. Said fifth nucleotide sequence is complimentary to at least a segment of said third nucleotide sequence. As a consequence, said fifth nucleotide sequence corresponds—at least in parts—to said first nucleotide sequence of said circular nucleic acid template. Ultimately, via the second nucleic acid concatemeric amplification product, the first nucleotide sequence of the circular nucleic acid template is immobilized to the solid support.

In another embodiment of the method according to the invention, the following further step is carried out:

vi) removing said at least one first nucleic acid concatemeric amplification product, preferably by denaturation.

By this measure a solid support is obtained which only comprises the at least one second nucleic acid concatemeric amplification product covalently linked to the at least one first nucleic acid immobilized primer. Such resulting solid support may be useful in any further molecular operation.

Preferably, the removal of said at least one first nucleic acid concatemeric amplification product is realized by the way of denaturation. The first nucleic acid concatemeric amplification product can then be washed from the solid surface. Now any desired further molecular operation involving the second nucleic acid concatemeric amplification product can be carried out. The second nucleic acid concatemeric amplification product is single stranded and comprises at least a segment of the first nucleotide sequence, i.e. the nucleotide sequence of the circular nucleic acid template in concatemeric form.

In another embodiment the method according to the invention comprises the following further step:

vii) detection of said at least one first nucleic acid concatemeric amplification product and/or said at least one second nucleic acid concatemeric amplification product.

By this measure the individual concatemeric amplification products which are spread over the solid support or its surface in a point-like manner can be identified. The detection can be realized in different ways known to the skilled person, for example by a sequencing reaction, the use of hybridization probes etc.

In another embodiment of the invention, at least one second nucleic acid immobilized primer having said second nucleotide sequence is linked to said solid support, wherein said at least one second nucleic acid immobilized primer comprises a removable modification at its 3' terminus blocking the addition of nucleotides, wherein preferably before and/or after step vii) said modification is removed from the 3' terminus of said at least one nucleic acid immobilized primer.

In said alternative embodiment said second nucleic acid immobilized primer corresponds to said first nucleic acid non-immobilized primer, however is linked to said solid support. The linkage of said second nucleic acid immobilized primer is preferably realized via its 5' terminus. The second nucleic acid primer comprises a removable or cleavable protective function at its 3' terminus which prevents a primer extension reaction. Such a linked second nucleic acid primer may undertake other tasks not associated with the amplification of the circular nucleic acid template. The protective function can be removed or cleaved-off at any step of the method according to the invention, e.g. before or after step vii), then making the second nucleic acid immobilized primer accessible for a primer extension reaction. This removal can be realized by adjusting appropriate reaction conditions such as temperature, pH value, addition of cleavage reagent, or enzymes such as uracil-N-glycosylase.

In another embodiment of the method according to the invention, step ii) and step iii) are executed in spatially separated compartments.

This measure has the advantage that the hybridization reaction and the complex formation occurring in step iv) can be controlled by the operating person. Only after subjecting of the first nucleic acid concatemeric amplification product resulting from step (ii) by the operating person to said solid support comprising the nucleic acid immobilized primer in step (iii), the complex formation can take place.

In another embodiment of the method according to the invention, step ii) and step iii) are executed in spatially connected compartments.

In this embodiment the RCA is directly taking place on or in close vicinity to the solid support or its surface, respectively. This measure has the advantage that there is no incubation time necessary resulting in a shortening of the duration of the entire method according to the invention.

In another embodiment of the method according to the invention said incubation in step ii) is realized for a time period of approx. 1 to 60 min, preferably of approx. 2 to 30 min, further preferably of approx. 5 to 20 min, and most preferably of approx. 15 min.

This embodiment is preferably realized in the variant of the method according to the invention where steps ii) and iii) are executed in spatially separated compartments. The indicated incubation times ensure a sufficient concentration of first nucleic acid concatemeric amplification products for the subsequent hybridization reaction in step iv).

In another embodiment of the method according to the invention said at least one nucleic acid non-immobilized primer and/or said at least one first nucleic acid immobilized primer and/or said at least one second immobilized primer comprise an exonuclease protecting modification at its 3' terminus, preferably a thioate bridge.

This measure increases the stability of the nucleic acid molecules against degradation by any exonuclease activity and, therefore, the effectivity of the entire method according to the invention.

In another embodiment of the method according to the invention said at least one nucleic acid non-immobilized primer and/or said at least one first nucleic acid immobilized primer comprise a modification selected from the group consisting of: a fluorophore, quencher, biotin, abasic site.

By this measure the indicated nucleic acid molecules can take over other or additional functionalities which may be helpful e.g. in the detection step vii) or any subsequent processing.

In another embodiment of the method according to the invention said at least one circular nucleic acid template is a single stranded nucleic acid, preferably a single stranded DNA.

Said measure has the advantage that no initiator protein is necessary which otherwise first has to nick one strand of the double stranded circular DNA molecule before the replication or amplification can begin.

In another embodiment of the method according to the invention said solid support comprises a material selected from the group consisting of: metal, glass, silica, plastics, and/or is preferably selected from the group consisting of: chips, beads, capillaries.

This measure has the advantage that the method according to the invention is adapted to any kind of material which is commonly used in molecular immobilization tasks.

Another subject matter of the invention relates to a nucleic acid non-immobilized primer in combination with nucleic acid immobilized primer linked to a solid support in the method according to the invention, preferably said nucleic acid non-immobilized primer and/or said nucleic acid immobilized primer comprise an exonuclease protecting modification at their 3' termini, further preferably a thioate bridge.

The features, characteristics, advantages and embodiments specified for the method according to the invention apply likewise to the use according to the invention.

It is to be understood that the before-mentioned features and those to be mentioned in the following cannot only be used in the combination indicated in the respective case, but also in other combinations or in an isolated manner without departing from the scope of the invention.

The invention is now further explained by means of embodiments resulting in additional features, characteristics and advantages of the invention. The embodiments are of pure illustrative nature and do not limit the scope or range of the invention. The features mentioned in the specific embodiments are general features of the invention which are not applicable in the specific embodiment but also in an isolated manner in the context of any embodiment of the invention.

The invention is now described and explained in further detail by referring to the following non-limiting examples and drawings.

Figure 2:
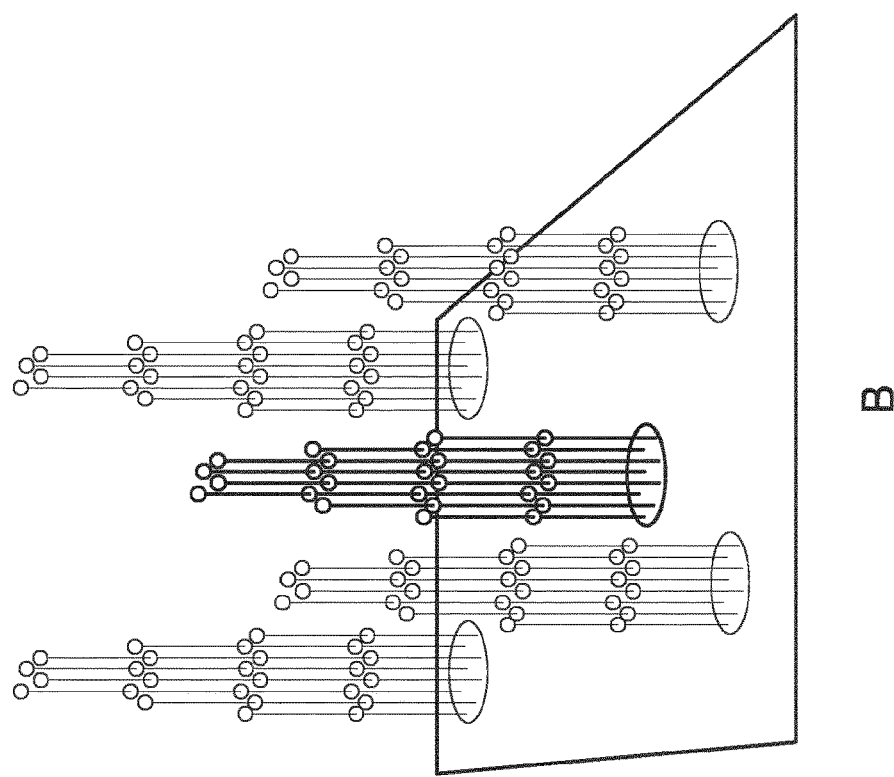
Figure 2:
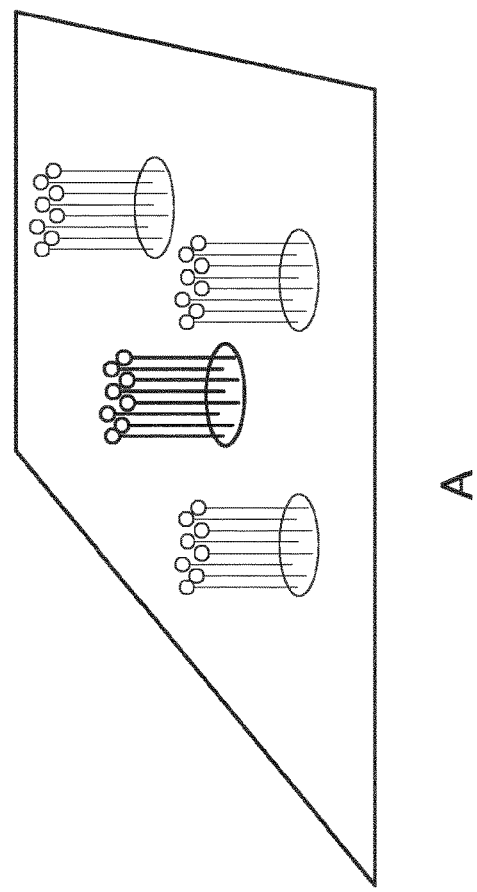
Figure 3:
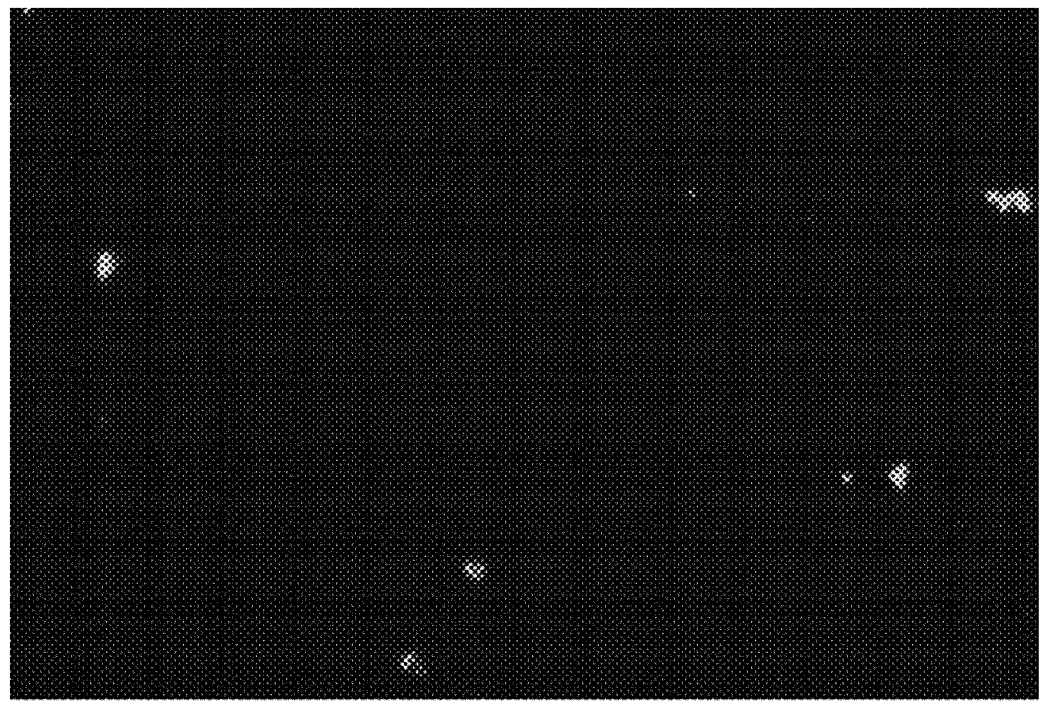
Figure 3:
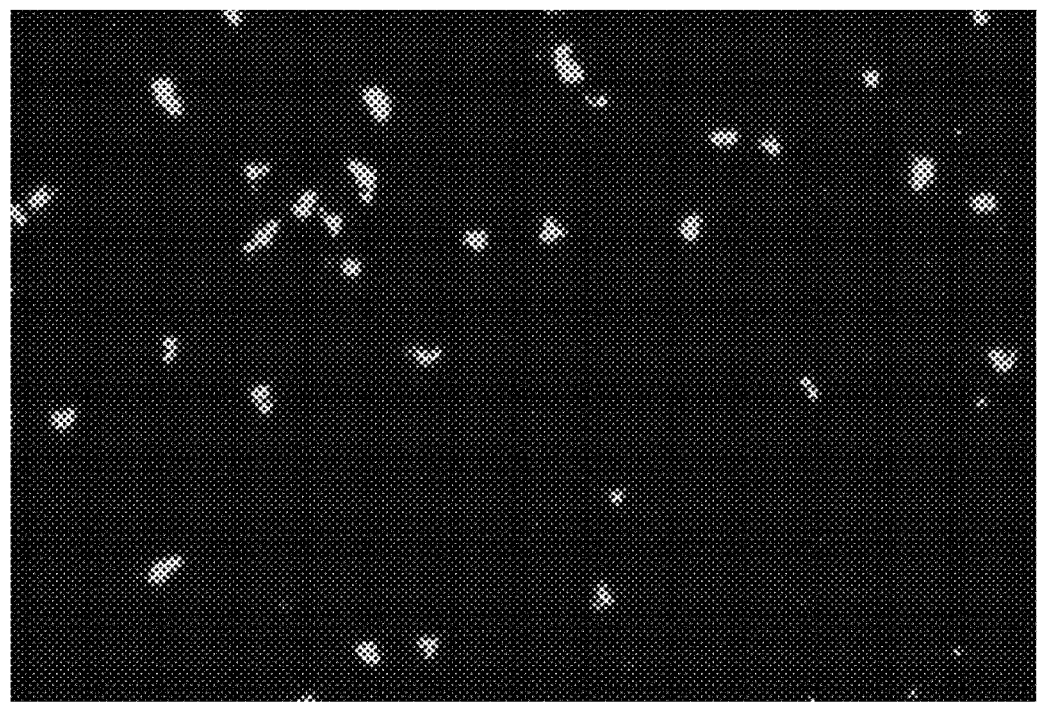
Figure 4:
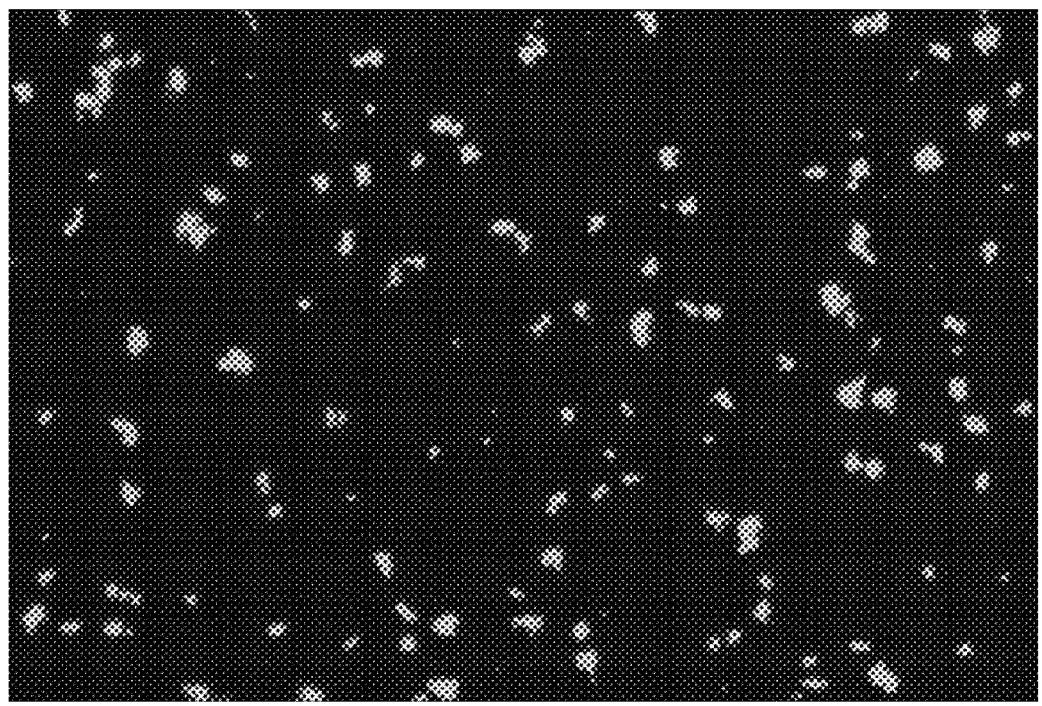
Figure 4:
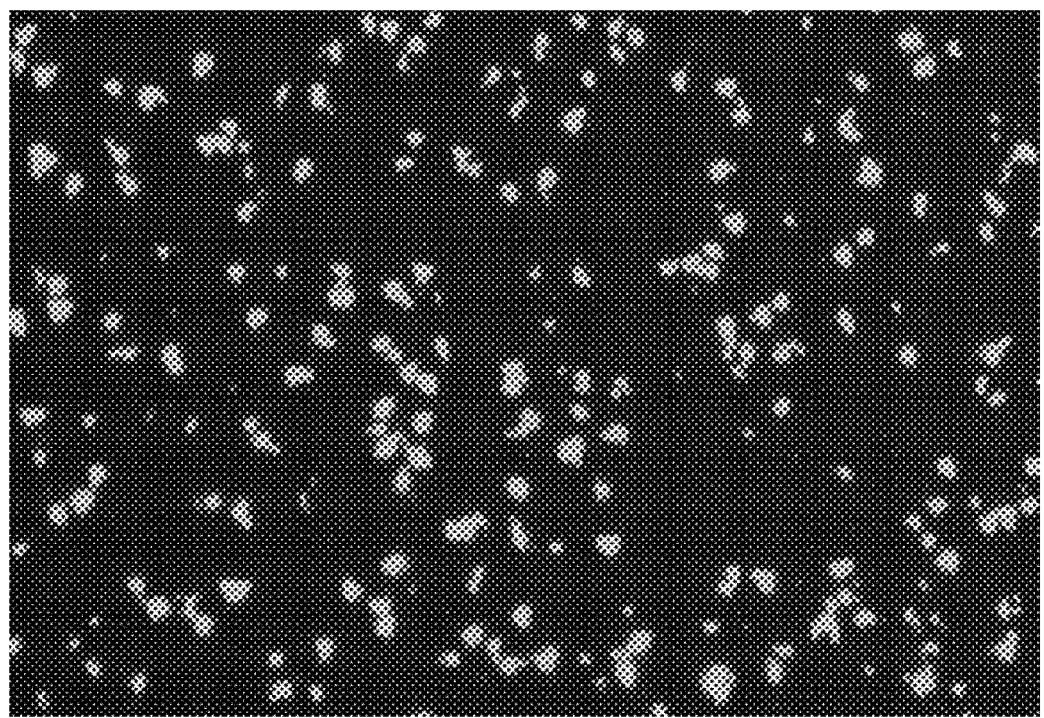

FIGS. 1(i) to 1(vii): shows a flow chart illustrating the method according to the invention. The first nucleotide sequence in FIG. 1(ii), the fourth nucleotide sequence in FIG. 1(iv), and the fifth nucleotide sequence in FIG. 1(v) are the same and set forth in SEQ ID NO:8. The second nucleotide sequence in FIG. 1(ii) and the third nucleotide sequence in FIGS. 1(ii), 1(iv) and 1(v) are the same and set forth in SEQ ID NO:9;

FIG. 2: shows the two-dimensional amplificate spreading in the art (A) versus three-dimensional amplificate spreading according to the invention (B). In the two-dimensional spreading the amplificate monomers are located next to each other. In the three-dimensional spreading the concatemeric amplificate monomers are also vertically arranged;

FIG. 3: shows the hybridization of the circle in the RCA mix without polymerase (A) and the hybridization of the concatemeric amplification product in the RCA mix with polymerase (B);

FIG. 4: shows the hybridization of the first concatemeric amplification product to the surface (34-fold magnification) (A); and the simultaneous reaction of the formation of the first concatemeric amplification product, the hybridization of the first concatemeric amplification product, and the multiple displacement amplification of the second concatemeric amplification product (34-fold magnification) (B).

EXAMPLES

1. Method According to the Invention

In FIG. 1 the individual steps of the method according to the invention are illustrated.

In step (i) the reaction mixture is provided comprising the circular nucleic acid template (1), in the following referred to as "circle", the strand displacement polymerase (2) and the nucleic acid non-immobilized primer (3). Not shown are the dNTPs and the reaction buffer.

In step (ii) the nucleic acid non-immobilized primer (3) anneals to the circle (1) and the rolling circle amplification can begin. The non-immobilized primer (3) is extended by the addition dNTPs to its 3' terminus. The circle (1) "rolls" due to the strand displacement function, thereby exposing continuously its sequence which serves as a continuous template for the primer extension. This reaction results in the first concatemeric amplification product (4) comprising multiple copies of the same sequence in a head-to-tail orientation. This configuration has significant advantages in the efficiency of the subsequent hybridization. After a short pre-incubation of the components of the reaction mixture for about 15 min, the reaction mixture can be subjected to a solid support (5) (step iii). Alternatively, the reaction mixture can be directly subjected to the solid support (5) (step (iii)). It is shown that the first nucleotide sequence ($1^{st}$ nt seq.) of the circle (1) (circ.) is at least partially complementary to the third nucleotide sequence ($3^{rd}$ nt seq.) of the first concatemeric amplification product (4) ($1^{st}$ concat.). The second nucleotide sequence ($2^{nd}$ nt seq.) of the nucleic acid non-immobilized primer (3) (non-imm. prim.) is also depicted in parts.

As shown in step (iii), the first nucleic acid immobilized primer (6) is provided in a form linked to the solid support (5).

In step (iv), the first concatemeric amplification product (4) anneals to the first immobilized primer (6) via hybridization of the complimentary bases of the first immobilized primer (6) and of the multiple copies of the first concatemeric amplification product (4), thereby immobilizing the first concatemeric amplification product (4) on the surface of the solid support (5). It is shown that the third nucleotide sequence ($3^{rd}$ nt seq.) of the first concatemeric amplification product (4) ($1^{st}$ concat.) is at least partially complementary to the fourth nucleotide sequence ($4^{th}$ nt seq.) of the first immobilized primer (6) (imm. prim.).

Meanwhile the RCA continues. The circle (1) and the strand displacement polymerase (2) as well as other required RCA components are still present.

The significant advantage is that the first amplification product (4) is a concatemer resulting in a much better hybridization in comparison to such of the circle (1) and a tighter anchoring.

Alternatively, not shown in FIG. 1, a 3' blocked second nucleic acid immobilized primer having the same nucleotide sequence as the first non-immobilized primer can be linked to the solid support which, however, does not contribute to the RCA but undertakes other functions. Before or after step (vii) a cleavage of the blocked second immobilized primer on the surface can take place. As the second immobilized primer comprises the same nucleotide sequence as the non-immobilized primer (3) after such cleavage, the first concatemeric amplification product (4) can be re-produced.

Alternatively, also not shown in FIG. 1, oligonucleotides can be immobilized on the surface of the solid support (5) comprise a cleavable function. In this embodiment, the RCA can continue on the surface in such a manner that the reaction conditions result in a cleavage of the oligonucleotides immobilized on the surface. For example, such reaction conditions can be of physical (e.g. temperature, chemical (pH, cleavage reagent) or biochemical nature (e.g. addition of enzymes such as uracil-N-glycosylase) in order to cleave the cleavable function.

In step (v), the generation of the second concatemeric amplification product (7) is shown. Since the linear first concatemeric amplification product (4) represents a target nucleic acid, the reaction mode changes from RCA to MDA (multiple displacement amplification). The reactions of steps (ii)-(iv) are not necessarily interrupted after the hybridization of the first concatemeric amplification product (4) to the first immobilized primer (6) at the surface of the solid support (5). It is shown that the third nucleotide sequence ($3^{rd}$ nt seq.) of the first concatemeric amplification product (4) ($1^{st}$ concat.) is at least partially complementary to the fifths nucleotide sequence ($5^{th}$ nt seq.) of the second concatemeric amplification product (7) ($2^{nd}$ concat.).

In step (vi), the first amplification product (4) was denaturated from the second amplification product (7). Whereas the second concatemeric amplification product (7) is covalently linked to the first immobilized primer (6), no such linkage exists for the first concatemeric amplification product (4). For this reason, the first concatemeric amplification product (4) can be removed from the surface (5) by a denaturation step.

In step (vii), the detection of the second amplification product (7) is shown. By this, the individual concatemeric amplification products (7) can be detected which are spread over the surface (5) in a spot-like manner. An exemplarily detection reaction is a sequencing reaction, a hybridization with sequence specific oligonucleotide probes (9) etc.

2. Experimental Validation 1

It should be demonstrated that the first concatemeric amplification product can be bound to a primer immobilized to a surface of a solid support with a higher efficiency and in the following can be effectively amplified by rolling circle amplification (RCA). A reaction serves as a control where the circles hybridize to a surface followed by an exponential RCA.

Streptavidin plades (StreptaWell strips, Roche) are coated for the control reaction with primer 1 for (sequence: biotin-aaa aaa aat tcg tat cct tgc gca get cg*a*g; SEQ ID NO:1), primer 1rev (sequence: biotin-aaa aaa aac cat gaa caa aat gtg act cat a*t*c; SEQ ID NO:2) and primer polyA (sequence: biotin-aaa aaa*a*a; SEQ ID NO:3). In the following 50 pg of the circle (sequence: atg acg ata tga gtc aca ttt tgt tca tgg gca tga cat tga tac aca gtt aga cga tag gac agt aca ttc gac cta tcc ttg cgc agc tcg aga tga cg; SEQ ID NO:4) are hybridized to the first primer immobilized on the surface of the solid support for 15 min at room temperature. Then the supernatant is removed, washed and dissolved in 50 μl of RCA reaction buffer (37 mM tris pH 7.5; 50 mM KCl; 10 mM $MgCl_2$, 20 mM $(NH_4)_2SO_4$, 1 mM dNTP mix, 1 μl REPLI-g Midi polymerase (φ29-DNA polymerase). In the following the reaction is carried out for 2 h at 38° C.

Alternatively for the test approaches the streptavidin plates are coated with the primer 1 for. 50 μl of RCA samples consist of 50 pg of circle, 37 mM tris pH 7.5; 50 mM KCl; 10 mM $MgCl_2$, 20 mM $(NH_4)_2SO_4$, 1 mM dNTP mix, 1 μl REPLI-g Midi polymerase (φ29-DNA polymerase) and first non-immobilized primer, and are pre-incubated for 5 min to 30 min at 30° C. before the RCA mixes are subjected to the surface of the streptavidin plates which were coated with the immobilized primer. In the following the reaction is carried out for 2 h at 38° C.

After the incubation for 2 h at 38° C. in the control sample as well as the test samples the supernatant is removed and the surface is washed. Then the DNA is treated on the surface with 50 μl of denaturation and lysis buffer (DLB) (from the REPLI-g Mini Kit). The treatment is stopped after 1 h at 37° C. with 50 μl of Stop Solution (from the REPLI-g Mini Kit). The supernatant now only contains DNA formerly immobilized on the surface. This DNA can now be detected in a real-time PCR (QuantiFast SYBR green kit) with the suitable primers [primer 2 forward: 5' ctg tgt atc aat gtc atg cc 3' (SEQ ID NO:5) and primer 2 reverse: 5' ggt aga cga tag gac agt aca 3' (SEQ ID NO:6)].

The position "*" in the oligonucleotides indicates that instead of a phosphate bridge a thioate bridge is provided between the sugar and the sugar phosphate backbone.

The result is shown in the following table 1.

TABLE 1

The CT values measured after the real-time PCR

|  | CT | Variation coefficient |
|---|---|---|
| Control | 16.53 | 0.015 |
| Test 5 min 30° C. | 14.83 | 0.008 |

TABLE 1-continued

The CT values measured after the real-time PCR

|  | CT | Variation coefficient |
|---|---|---|
| Test 10 min 30° C. | 14.58 | 0.006 |
| Text 20 min 30° C. | 14.25 | 0.025 |
| Test 30 min 30° C. | 14.91 | 0.012 |

The table clearly shows lower CT values for the test samples where the first concatemeric amplification product is generated in solution and not on the surface of the solid support and is only immobilized on the surface via the immobilized primer. The CT values are 1.6 to 2.3 cycles lower. This corresponds to an approximately 3 to 4.8-fold improvement of the binding of the sequence to the surface of the solid support.

3. Experimental Validation 2

It should be demonstrated that the first concatemeric amplification products can be bound to primers immobilized to a surface of a solid support with a higher efficiency and in the following can be amplified by rolling circle amplification (RCA) in an efficient manner. As a control, a reaction is used where the circles without previous RCA hybridized to the surface of the solid support and only then a RCA is carried out.

Streptavidin coated glass slides coated with primer 1 for (SEQ ID NO:1) and primer poly A (SEQ ID NO:3) were covered with a RCA mixture. The RCA mixture consisted of 50 pg of a circular DNA (SEQ ID NO:4) in 50 μl of RCA mix consisting of dNTPs, buffer and primer (sequence 5'-aaa tgt gac tca ta*t*c-3'; SEQ ID NO:7). Two preparations were tested:

1) In the first preparation the surface was covered with the described mixture and incubated for hybridization for 15 min. In the following, nonbound circle was washed away. The surface was then incubated with an RCA mixture without any primer, but containing polymerase and dNTPs and was incubated for 2 h at 38° C.

2) In the second preparation the surface was covered with the described mixture, wherein 1 ml of REPLI-g midi polymerase (φ29 polymerase) was added. In the following, for the RCA pre-amplification and the hybridization of the first concatemeric amplification product, incubation for 10 min at 30° C. was carried out. The mixture was removed and the surface was washed as under 1). In the following the surface was covered with RCA mixture without any primer, but still containing polymerase and dNTPs, and incubated for 2 h at 38° C.

In the following, the RCA mixtures of both surfaces were removed and the surfaces were covered with a 1:10,000 YOYO®-1 iodide solution and incubated for 30 min. After the surface was washed, the glass slide was scanned.

The result is shown in FIG. 3. There areas of the scanned glass slides are depicted. The hybridization and RCA events are represented by small spots. The image clearly illustrates that with a previous formation of the first concatemeric amplification product (FIG. 3B) clearly more hybridization events take place than in the case where no concatemeric amplification product is generated (FIG. 3A).

4. Experimental Validation 3

It should be demonstrated that a separate hybridization of the first concatemeric amplification product is not necessary and, therefore, the step of hybridization of the circular DNA can be saved.

Streptavidin coated glass slides which were covered with primer 1 for (SEQ ID NO:1) and poly A (SEQ ID NO:3) were covered with a RCA mixture. Two preparations were used:

1) In the first (and in the second preparation) the RCA mixture consisted of 50 pg of a circular DNA (SEQ ID NO:4), buffer, primer (SEQ ID NO:7) and REPLI-g Midi Polymerase (φ29 polymerase). In the first sample, before the covering of the surface, the formation of the first concatemeric amplification product was generated independently from the surface of the solid support for 10 min at 30° C. After the incubation, the surface was covered with the first concatemeric amplification reaction and incubated for additional 2 h at 38° C. In the following, the reaction was stopped by incubation at 65° C. for 5 min.

2) In the second preparation a simultaneous reaction of the formation of the first concatemeric amplification product, of the hybridization of the first concatemeric amplification product, and the subsequent MDA for the formation of the second concatemeric amplification product was carried out on the surface of the solid support for 2 h at 38° C. Then the reaction was stopped by incubation at 65° C. for 5 min. By this, the time for the hybridization can be saved.

In the following, the RCA mixtures of both surfaces were removed and the surfaces were covered with a 1:10,000 YOYO®-1 iodide solution and incubated for 30 min. After washing the surfaces, the glass slides were scanned.

The result is shown in FIG. 4. There areas of the scanned glass slides are depicted. The hybridization and RCA events are shown as small spots. Surprisingly, the scans clearly show that even more spots (hybridization and amplification events) can be seen if simultaneously (a) the first concatemeric amplification product is generated, (b) the first concatemeric amplification product is hybridized to the surface, and (c) the MDA reaction is carried out for the generation of the second concatemeric amplification product (FIG. 4B) in comparison to a separate carrying out of such steps (FIG. 4A).

| Sequences |
|---|
| SEQ ID NO: 1 |
| aaaaaaaatt cgtatccttg cgcagctcga g |
| |
| SEQ ID NO: 2 |
| aaaaaaaacc atgaacaaaa tgtgactcat atc |
| |
| SEQ ID NO: 3 |
| aaaaaaaa |
| |
| SEQ ID NO: 4 |
| atgacgatat gagtcacatt ttgttcatgg gcatgacatt gatacacagt tagacgatag gacagtacat tcgacctatc cttgcgcagc tcgagatgac g |
| |
| SEQ ID NO: 5 |
| ctgtgtatca atgtcatgcc |
| |
| SEQ ID NO: 6 |
| ggtagacgat aggacagtac a |
| |
| SEQ ID NO: 7 |
| aaatgtgact catatc |

The invention claimed is:

1. A method for nucleic acid immobilization, comprising:
   i) providing a reaction mixture comprising
      at least one circular nucleic acid template having a first nucleotide target sequence;
      at least one strand displacement polymerase;
      deoxynucleoside triphosphates (dNTPs);
      reaction buffer, and
      at least one nucleic acid non-immobilized primer having a second nucleotide sequence, said second nucleotide sequence being complementary to at least a segment of said first nucleotide target sequence;
   ii) incubating said reaction mixture under conditions allowing
      said at least one nucleic acid non-immobilized primer to anneal to said at least one circular nucleic acid template, and
      synthesizing at least one first nucleic acid concatemeric amplification product by extending said at least one nucleic acid non-immobilized primer by rolling circle amplification (RCA), said at least one first nucleic acid concatemeric amplification product comprises multiple copies of a third nucleotide sequence in a head-to-tail orientation, said third nucleotide sequence being complementary to at least a segment of said first nucleotide target sequence;
   iii) providing at least one first nucleic acid immobilized primer having a fourth nucleotide sequence linked to a solid support, said fourth nucleotide sequence being complementary to at least a segment of said third nucleotide sequence;
   iv) allowing said at least one first nucleic acid concatemeric amplification product to anneal to said at least one first nucleic acid immobilized primer and obtaining at least one first nucleic acid concatemeric amplification product-first nucleic acid immobilized primer complex immobilized to said solid support; and
   v) incubating said at least one first nucleic acid concatemeric amplification product-first nucleic acid immobilized primer complex under conditions and synthesizing at least one second nucleic said concatemeric amplification product by extending said first nucleic acid immobilized primer in the presence of said strand displacement polymerase, said at least one second nucleic said concatemeric amplification product comprises multiple copies of a fifth nucleotide sequence in a head-to-tail orientation, said fifth nucleotide sequence being complementary to at least a segment of said third nucleotide sequence, thereby forming a hybrid of the first nucleic acid concatemeric amplification product and the second nucleic acid concatemeric amplification product.

2. The method of claim 1, comprising the following further step:
   vi) removing said at least one first nucleic acid concatemeric amplification product from the solid support.

3. The method of claim 2, wherein step vi) is performed by denaturing the hybrid of the first nucleic acid concatemeric amplification product and the second nucleic acid concatemeric amplification product.

4. The method of claim 1, comprising the following further step:
   vii) detecting said at least one first nucleic acid concatemeric amplification product and/or said at least one second nucleic acid concatemeric amplification product.

5. The method of claim 4, further comprising at least one second nucleic acid immobilized primer having said second nucleotide sequence linked to said solid support, wherein said at least one second nucleic acid immobilized primer comprises a removable modification at its 3' terminus which blocks the addition of nucleotides to said 3' terminus, and wherein before or after step vii) said modification is removed from the 3' terminus of said at least one second nucleic acid immobilized primer.

6. The method of claim 1, further comprising at least one second nucleic acid immobilized primer having said second nucleotide sequence linked to said solid support, wherein said at least one second nucleic acid immobilized primer comprises a removable modification at its 3' terminus which blocks the addition of nucleotides to said 3' terminus.

7. The method of claim 6, wherein said at least one nucleic acid non-immobilized primer and/or said at least one first nucleic acid immobilized primer and/or said at least one second immobilized primer comprise/comprises an exonuclease protecting modification at its 3' terminus or their 3' termini.

8. The method of claim 7, wherein said exonuclease protecting modification comprises a thioate bridge.

9. The method of claim 1, wherein step ii) and step iii) are executed in spatially separated compartments.

10. The method of claim 1, wherein step ii) and step iii) are executed in spatially connected compartments.

11. The method of claim 1, wherein step ii) is performed for a time period from approximate 1 minute to 60 minutes.

12. The method of claim 1, wherein said at least one nucleic acid non-immobilized primer and/or said at least one first nucleic acid immobilized primer comprise/comprises an exonuclease protecting modification at its 3' terminus or their 3' termini.

13. The method of claim 12, wherein said exonuclease protecting modification comprises a thioate bridge.

14. The method of claim 1, wherein said at least one nucleic acid non-immobilized primer and/or said at least one first nucleic acid immobilized primer comprise/comprises a modification selected from the group consisting of: a fluorophore, a quencher, a biotin, and an abasic site.

15. The method of claim 1, wherein said at least one circular nucleic acid template is a single stranded nucleic acid.

16. The method of claim 1, wherein said solid support comprises a material selected from the group consisting of: metal, glass, silica, and plastics.

17. The method of claim 1, wherein step ii) is performed for a time period from approximate 2 minutes to 30 minutes.

18. The method of claim 1, wherein step ii) is performed for a time period from approximate 5 minutes to 20 minutes.

19. The method of claim 1, wherein step ii) is performed for a time period of approximate 15 minutes.

20. The method of claim 1, wherein said at least one circular nucleic acid template is a single stranded DNA.

21. The method of claim 1, wherein said solid support is selected from the group consisting of: chips, beads, and capillaries.

* * * * *

SEQUENCE LISTING

```
<160> NUMBER OF SEQ ID NOS: 9

<210> SEQ ID NO 1
<211> LENGTH: 31
<212> TYPE: DNA
<213> ORGANISM: Artificial Sequence
<220> FEATURE:
<223> OTHER INFORMATION: primer 1 for

<400> SEQUENCE: 1
aaaaaaaatt cgtatccttg cgcagctcga g                              31

<210> SEQ ID NO 2
<211> LENGTH: 33
<212> TYPE: DNA
<213> ORGANISM: Artificial Sequence
<220> FEATURE:
<223> OTHER INFORMATION: primer 1 rev

<400> SEQUENCE: 2
aaaaaaaacc atgaacaaaa tgtgactcat atc                            33

<210> SEQ ID NO 3
<211> LENGTH: 8
<212> TYPE: DNA
<213> ORGANISM: Artificial Sequence
<220> FEATURE:
<223> OTHER INFORMATION: primer poly A
```

```
<400> SEQUENCE: 3
aaaaaaaa                                                                 08

<210> SEQ ID NO 4
<211> LENGTH: 101
<212> TYPE: DNA
<213> ORGANISM: Artificial Sequence
<220> FEATURE:
<223> OTHER INFORMATION: circle

<400> SEQUENCE: 4
atgacgatat gagtcacatt ttgttcatgg gcatgacatt gatacacagt tagacgatag     60
gacagtacat tcgacctatc cttgcgcagc tcgagatgac g                        101

<210> SEQ ID NO 5
<211> LENGTH: 20
<212> TYPE: DNA
<213> ORGANISM: Artificial Sequence
<220> FEATURE:
<223> OTHER INFORMATION: primer 2 forward

<400> SEQUENCE: 5
ctgtgtatca atgtcatgcc                                                    20

<210> SEQ ID NO 6
<211> LENGTH: 21
<212> TYPE: DNA
<213> ORGANISM: Artificial Sequence
<220> FEATURE:
<223> OTHER INFORMATION: primer 2 reverse

<400> SEQUENCE: 6
ggtagacgat aggacagtac a                                                  21

<210> SEQ ID NO 7
<211> LENGTH: 16
<212> TYPE: DNA
<213> ORGANISM: Artificial Sequence
<220> FEATURE:
<223> OTHER INFORMATION: primer

<400> SEQUENCE: 7
aaatgtgact catatc                                                        16

<210> SEQ ID NO 8
<211> LENGTH: 15
<212> TYPE: DNA
<213> ORGANISM: Artificial Sequence
<220> FEATURE:
<223> OTHER INFORMATION: Synthetic sequence

<400> SEQUENCE: 8
atcgcactga acgcg                                                         15

<210> SEQ ID NO 9
<211> LENGTH: 15
<212> TYPE: DNA
<213> ORGANISM: Artificial Sequence
<220> FEATURE:
<223> OTHER INFORMATION: Synthetic sequence

<400> SEQUENCE: 9
cgcgttcagt gcgat                                                         15
```